United States Patent [19]
Salter et al.

[11] Patent Number: 5,573,280
[45] Date of Patent: Nov. 12, 1996

[54] TUBING END-PIECE AND CONNECTOR

[75] Inventors: Peter W. Salter, Tehachapi; James N. Curti, Bakersfield; Duane D. Kazal, Tehachapi; Laurence McGann, Woodland Hills, all of Calif.

[73] Assignee: Salter Labs, Arvin, Calif.

[21] Appl. No.: 395,984

[22] Filed: Feb. 28, 1995

[51] Int. Cl.$^6$ ........................................ F16L 35/00
[52] U.S. Cl. ..................... 285/38; 285/93; 285/239; 285/305; 285/397; 285/276
[58] Field of Search ........................ 285/38, 239, 305, 285/8, 397, 370, 93, 332.4, 276

[56] References Cited

U.S. PATENT DOCUMENTS

| | | | |
|---|---|---|---|
| Re. 32,482 | 8/1987 | Anderson | 285/38 X |
| 2,071,780 | 2/1937 | Aghnides | 285/8 |
| 2,071,842 | 2/1937 | Kennedy | 285/8 |
| 2,085,841 | 7/1937 | Weiss | 285/8 |
| 3,413,017 | 11/1968 | Hughey | 285/38 |
| 4,443,028 | 4/1984 | Hayes | 285/38 |
| 4,597,594 | 7/1986 | Kalalieff | 285/239 |
| 4,635,972 | 1/1987 | Lyall | 285/397 X |
| 4,783,099 | 11/1988 | Muser | 285/93 X |

FOREIGN PATENT DOCUMENTS

| | | | |
|---|---|---|---|
| 1428557 | 1/1966 | France | 285/8 |
| 686315 | 1/1953 | United Kingdom | 285/8 |

Primary Examiner—Dave W. Arola
Attorney, Agent, or Firm—Shoemaker and Mattare, Ltd.

[57] ABSTRACT

A tubing end-piece interconnects a free end of a piece of tubing and a tubing connector or fitting so that a fluid can flow between the tubing and the fitting or connector. The tubing end-piece includes a body member extending along a longitudinal axis with a bore extending longitudinally therethrough. The body member has an elongated body portion, a doughnut-shaped head portion and a frustoconically-shaped tail portion. The body portion has an outer body surface configured in a shape of a frustum that tapers from a first end and towards a second end. The doughnut-shaped head portion is connected to the first end of said body portion and extends radially outwardly relative to the longitudinal axis to form in cross-section an outer curved surface commencing from the first end and terminating in an outer peripheral edge which defines a first opening into the bore. A frustoconically-shaped tail portion is connected to the second end of the body portion and tapers from the second end and towards a second opening into the bore. The body member has an inner first surface and an inner second surface defining the bore and has a plurality of splines which are spaced apart from one another and extend longitudinally along and outwardly from the outer body surface. The present invention also includes a connector adapted to interconnect a pair of tubing end-pieces so that the fluid can flow between and through the respective pieces of tubing and the pair of tubing connectors, and present a connection which resists snagging when trailed from a portable or fixed source of oxygen gas to an ambulatory patient.

2 Claims, 10 Drawing Sheets

TUBING END-PIECE AND CONNECTOR

FIELD OF THE INVENTION

The present invention relates to a tubing end-piece for use to connect tubing together. More particularly, the present invention is directed to a tubing end-piece body adapted to finish the end of a tubing so that it can be connected to tubing connectors. In turn, the connected tubing, end-piece and tubing connector will provide fluid tight communication for fluid flow therethrough.

BACKGROUND OF THE INVENTION

Although numerous ways are employed to connect tubing together, or to connect tubing to apparatus fittings and the like is to provide the tubing with an elastomeric end-piece. Most typically the end-piece is adhesively affixed to one of the free ends of the tubing.

Tubing fabricated from a stiff yet pliable material such as polyvinylchloride plastic is used extensively in the health care industry. Such tubing is used to convey oxygen from portable oxygen source to ambulatory patients who suffer from respiratory illnesses or to convey intravenous solutions from containers and into patients for various medical reasons. Prior art tubing end-pieces and connectors are adequate to connect together two pieces of tubing in a fluid tight connection. Unfortunately, with ambulatory patients, these tubing end-pieces can become caught with furniture, under doors or in other places when a patient moves from one place to another. When this occurs, the ambulatory patient might cause one of the free ends of the tubing to disengage from any device to which the tubing may previously be connected to or catch and cause patient discomfort.

Typically, the prior art tubing end-pieces were fabricated from a stiff yet resilient material and included a body member having an elongated cylindrically-shaped body portion and a cylindrically-shaped head portion with a diameter larger than the body portion. These cylindrically-shaped portions of the tubing end-piece contributed to the problem of catching on furniture, under doors or in other items. A cylindrically-shaped bore extends longitudinally through both the body portion and the head portion. The head portion is used to assist in urging the tubing connector into engagement with a fitting. Although it is helpful to twist the prior art tubing end-piece while urging it into engagement with the fitting, gripping the tubing connector to obtain sufficient twisting force may cause the body portion to collapse. Thus, twisting a prior art tubing end-piece may have to be done carefully when attempting to engage a fitting because the fitting is cylindrical while the collapsed body portion may deform the cylindrically-shaped bore into an oval shape.

A need, therefore, exists to provide a tubing end-piece that is configured in a manner to avoid becoming caught with furniture, under doors or with other items while being moved by the patient. There is another need to provide an improved tubing end-piece so that is can be twisted while being connected to a fitting. There is likewise a need for a rigid tubing connector to releasably connect two tubing end-pieces together in the fluid tight relationship.

OBJECTS OF THE INVENTION

It is an object of the present invention to provide a new and useful tubing end-piece and combination of end-piece and connector combined which are configured in a manner to reduce the possibility of becoming caught with furniture, under doors or on other items.

It is another object of the present invention to provide a tubing end-piece and end-piece connector wherein the end-piece is sufficiently rigid and configured in a manner so that when urging the tubing end-piece onto a relatively rigid tubing connector or a fitting the bore of the end-piece resists substantial deformation.

It is yet another object of the present invention to provide a tubing connector within enhance gripping characteristics so that so that the tubing end-piece can be easily gripped when twisting onto or off of a free end of tubing connector or a fitting.

It is a further object of the present invention to provide a tubing end-piece and connector that is effective in use and simple and inexpensive to manufacture.

These and other objects of the present invention will become more readily appreciated and understood from consideration of the following detailed description of the exemplary embodiments of the present invention when taken in conjunction with the accompanying drawings.

SUMMARY OF THE INVENTION

Accordingly, the tubing end-piece and connector of the present invention is described which is adapted to interconnect a first free end of a first piece of tubing and a second free end of a second piece of tubing so that a fluid can flow through the first and second pieces of the tubing when interconnected by the use of plural end-pieces and a connector. The tubing end-piece of the present invention includes a body member extending along a longitudinal axis with a bore extending longitudinally therethrough. The body member includes an elongated body portion, a doughnut-shaped head portion and a frustoconically-shaped tail portion. The body portion has an outer body surface configured in a shape of a frustum that tapers from a first end and towards a second end. The doughnut-shaped head portion is connected to the first end of said body portion and extends radially outwardly relative to the longitudinal axis to form in cross-section an outer curved surface commencing from the first end and terminating in an outer peripheral edge which defines a first opening into the bore. The first opening is sized and adapted to slidably removably receive and retain the tubing connector described herein, and the second opening is sized to permanently receive the free end of a piece of tubing in a close-fitting relationship. A frustoconically-shaped tail portion is connected to the second end of the body portion and tapers from the second end and towards a second opening into the bore. The second opening is sized and adapted to slidably receive and retain in a close-fitting relationship a free end of a piece of tubing or a tubing fitting or tubing connector, all of which hereinafter will be referred to as tubing.

The body member includes an inner first surface and an inner second surface defining the bore. The inner first surface is disposed centrally about the longitudinal axis and forms a frustoconically-shaped first bore region converging inwardly from the first opening and through the head portion. The inner second surface is disposed centrally about the longitudinal axis and forms a frustoconically-shaped second bore region converging inwardly from the second opening and through the tail portion and the body portion. A ridge element is connected to and extends circumferentially about the inner second surface and is disposed substantially midway between the first and second openings. A plurality of splines are spaced apart from one another and extend longitudinally along the outer body surface of the body portion. Each of the splines are connected to the outer body surface of the body portion and the curved surface of the head portion. The body member is fabricated of unitary construction and from a stiff yet resilient material. The stiff yet resilient material is selected from a group consisting of rubber and plastic and, most preferably polyvinylchloride. It is preferred that the stiff yet pliable material is transparent or translucent.

Also, a connector is described which is used in combination with a pair of tubing end-pieces described herein with each end-piece being connected to a respective free end of a piece of tubing. The connector is adapted to interconnect or couple the pair of tubing end-pieces so that the fluid can flow between and through the respective pieces of tubing. The connector for coupling the end-pieces includes a body structure and a pair of tube structures. The body structure extends along a longitudinal axis from a first end to a second end and has a hole extending longitudinally therethrough and between the first and second ends. The hole is oriented centrally about the longitudinal axis. The body structure also has an outer body surface which extends longitudinally along and is disposed radially from the longitudinal axis at a first radial distance.

Each of the tube structures defines a conduit extending therethrough and has a distal end and a proximal end. Each of said tube structures is connected to a respective one of the first and second ends of the body structure at the proximal end in a manner whereby the conduit is oriented centrally about the longitudinal axis. The conduits and the hole form a continuous passageway between the distal ends of the pair of tube structures and through the pair of tube structures and the body structure. Each of the tube structures has an outer tube surface extending longitudinally along and radially from the longitudinal axis at a second radial distance. The first radial distance is greater than the second radial distance.

The body structure is generally cylindrically shaped and includes a pair of conical end portions. Each of the conical end portions tapers from the outer body surface towards a respective one of the first and second ends. The outer body surface also includes a plurality of ridges which extend longitudinally therealong and project radially outwardly therefrom. Each of the ridges is configured in cross-section in a shape of an inverted "V" and consecutive ones of the plurality of inverted V-shaped ridges are spaced apart from one another by a V-shaped channel which extends longitudinally along the outer body surface. Preferably, the body structure and the pair of tube structures are of unitary construction. It is also preferred that the body structure as well as the pair of tube structures are fabricated from a stiffer material than the end-pieces.

Each of the tube structures includes a plurality of collars that connect to and extend circumferentially about and radially outwardly from the outer tube surface. The plurality of collars are spaced apart from one another to define an annularly-shaped channel disposed between consecutive ones of the collars. Each of the tube structures also includes a frustoconically-shaped head member which is disposed on and extends circumferentially about the outer tube surface. The head member commences at the distal end and diverges outwardly toward the body structure.

DETAILED DESCRIPTION OF THE EMBODIMENTS

A tubing end-piece of the present invention is adapted to interconnect and provide a fluid tight connection between two pieces of tubing or a piece of tubing and a tubing connector or fitting so that a fluid can flow through the pieces of the interconnected tubing or to a fitting. It can be appreciated that the tubing described herein can be made from materials which produce a stiff yet resilient flexible tubing such as transparent or translucent tubing used in health care applications or rigid tubing fabricated from metal. The tubing can also be end portions of tubing projecting from fitting assemblies such as valves operably connected to tanks or other equipment. Furthermore, the stiff yet resilient tubing or the rigid tubing could be either removably force-fitted into the tubing connector of the present invention or permanently affixed to the tubing end-pieces described herein. One common arrangement is found in the health care industry where an ambulatory patient pulls or carries an oxygen concentrator or supply tank of gas or liquefied gas. Here, the first free end of a piece of tubing fabricated from a stiff yet resilient material is permanently affixed to one end of the tubing connector by an adhesive and a second piece of tubing fabricated from a metal which projects from a valve fitting assembly on the oxygen concentrator is removably connected to the tubing end-piece at an opposite end. This arrangement affords the patient to simply and easily remove or connect the tubing connector from the oxygen concentrator when desired, which is commonly referred to in the industry as a "quick disconnect".

Figure 1:
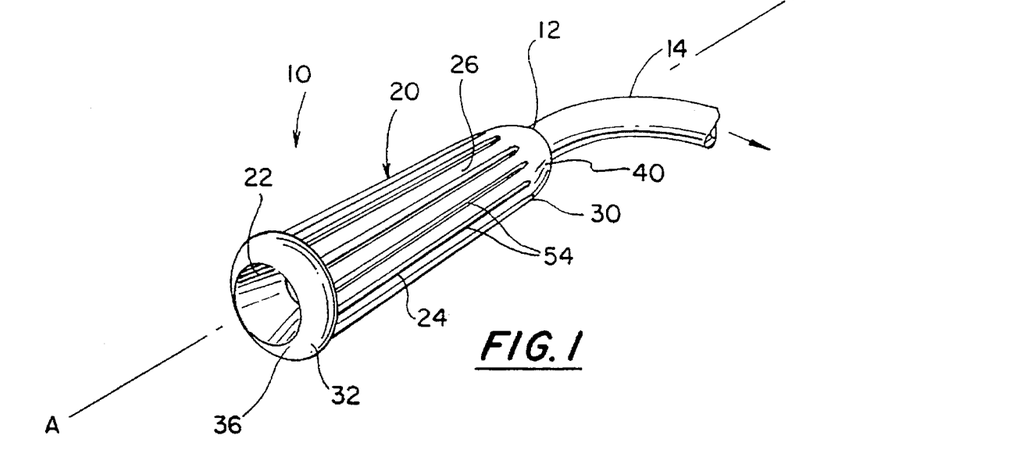
FIG. 1 is a perspective view of a preferred embodiment of a tubing end-piece of the present invention.

A tubing end-piece 10 of the present invention is generally introduced in FIGS. 1–4. In FIG. 1, tubing end-piece 10 receives free end 12 of a piece of tubing 14. Tubing connector 10 includes a body member 20 which extends along a longitudinal axis "A" with a bore 22 extending longitudinally therethrough. Body member 20 includes an elongated body portion 24 having an outer body surface 26 configured in a shape of a frustum tapering from a first end 28 and towards a second end 30. A doughnut-shaped head portion 32 is connected to first end 28 of body portion 24 and extends radially outwardly relative to longitudinal axis "A" to form in cross-section an outer curved surface 34 commencing from first end 28 and terminating in an outer peripheral edge 36. Outer peripheral edge 36 defines a first opening 38 into bore 22. First opening 38 is sized and adapted to slidably receive and retain a free end 12 of piece of tubing 14 in a close-fitting relationship. The first opening 38 should be sized and adapted to slidably receive and retain one tubular end of the connector shown in FIGS. 5, 6, and 10. A frustoconically-shaped tail portion 40 (FIG. 2) is connected to second end 30 of body portion 24 and tapers from second end 30 and towards a second opening 42 into bore 22. Second opening 42 is sized and adapted to slidably receive and permanently retain a free end 16 of piece of tubing 18 in a close-fitting relationship.

Figure 2:
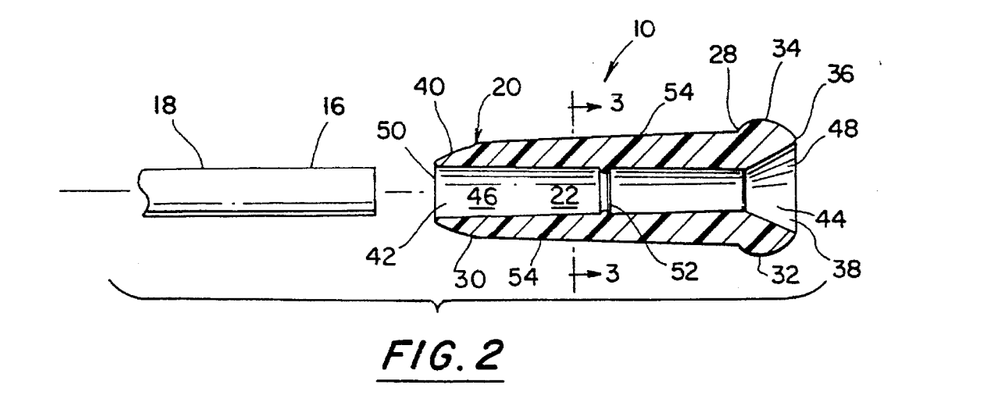
FIG. 2 is a cross-sectional view in elevation of the tubing end-piece of the present invention shown in FIG. 1.
Figure 3:
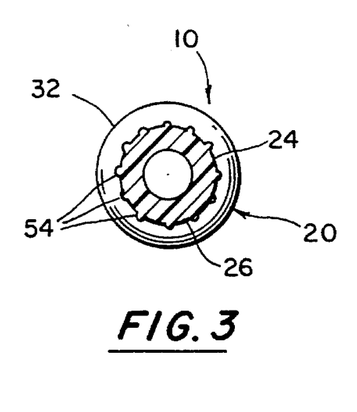
FIG. 3 is a cross-sectional view in elevation of the tubing end-piece of the present invention taken along line 3—3 shown in FIG. 2.
Figure 4:
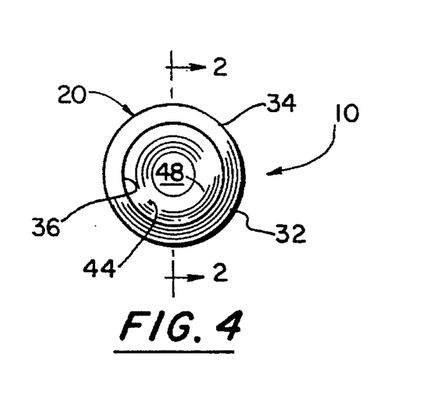
FIG. 4 is a front elevational view of a head portion of the tubing connector of the present invention.

Body member 20 includes an inner first surface 44 and an inner second surface 46 which define bore 22. Inner first surface 44 is disposed centrally about longitudinal axis "A" and forms a frustoconically-shaped first bore region 48 which converges inwardly from first opening 38 and through head portion 32. Inner second surface 46 is disposed centrally about longitudinal axis "A" and forms a frustoconically-shaped second bore region 50 which converges inwardly from second opening 42 and through tail portion 40 and body portion 24.

Tubing end-piece 10 also includes a ridge element 52 which is connected to and extends circumferentially about inner second surface 46. Ridge element 52 is disposed substantially midway between first and second openings 38 and 42 respectively. Ridge element 52 acts as a stop to prevent the free end of the tubing from advancing there beyond when inserted into the bore.

Tubing end-piece 10 further includes a plurality of splines 54 which are spaced apart from one another and extend longitudinally along outer body surface 26 of body portion 24. Each of splines 54 is connected to outer body surface 26 of body portion 24 and outer curved surface 34 of said head portion 32. Splines 54 add rigidity to tubing connector 10 and also provide additional frictional characteristics thus allowing twisting of tubing connector 10 when engaging a free end of tubing.

Although not by way of limitation, it is preferred that body member 20 is fabricated of unitary construction. Again, not by way of limitation, flexible body member 20 is fabricated from a stiff yet resilient material selected from a group consisting of various rubber or plastic compositions. It is further preferred that the stiff yet resilient material is transparent or translucent. Having a tubing end-piece fabricated from a transparent or translucent material enables a user to visually determine that, when engaging free ends of tubing with tubing end-piece 10, the free ends are appropriately inserted into the bore and in abutment with the ridge element.

Both the body portion and the tail portion of the tubing end-piece of the present invention are configured to taper. The head portion of the tubing end-piece has a doughnut-shaped configuration. These configurations of the tubing end-piece enable it to avoid becoming caught with furniture, under doors and in other items. With the splines, the tubing end-piece is sufficiently rigid so that when urging the tubing end-piece onto a tubing connector or a fitting, the bore resists deformation. Thus, the tubing end-piece of the present invention is easier to install onto the free end of a tubing connection or a valve fitting. Furthermore, the tubing end-piece of the present invention has enhanced gripping characteristics because of the splines. Now, the tubing connector can be more easily gripped so that it can be twisted onto or off of a free end of a tubing connector. Lastly, a skilled artisan would appreciate that the tubing end-piece of the present invention is effective in use and simple and inexpensive to manufacture.

A first exemplary embodiment of the connector 210 of the present invention is generally introduced in FIGS. 5–8. Connector 210 is used in combination with a pair of tubing end-pieces 10 such as ones described hereinabove or some other type tubing end-pieces of similar construction. By way of example only, the description of the exemplary embodiments of connector 210 shall be explained by incorporating tubing end-piece 10 of the present invention as heretofore described. Each tubing end-piece 10 is connected to the free end 16 of tubing 18 and has first opening 38 into bore 22 wherein the fluid (shown as arrows in FIG. 8) can flow through respective ones of tubing end-piece 10 and a connector or tubing 18. Connector 210 is adapted to interconnect the pair of tubing end-pieces 10 so that the fluid can flow between and through the respective pieces of tubing 14 and 18 (see FIG. 6). Connector 210 includes a body structure 212 and a pair of tube structures 214.

Figure 5:
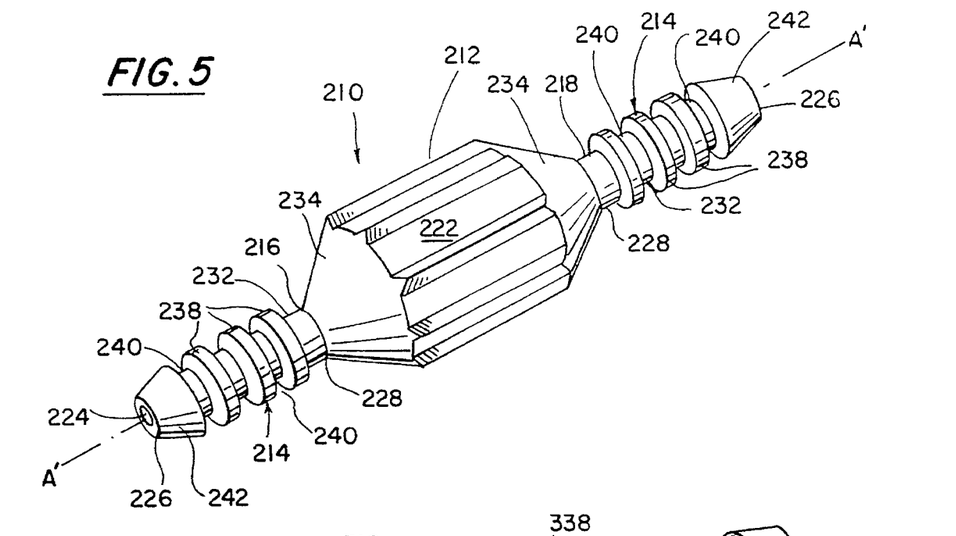
FIG. 5 is a perspective view of a first exemplary embodiment of a connector according to the present invention.
Figure 6:
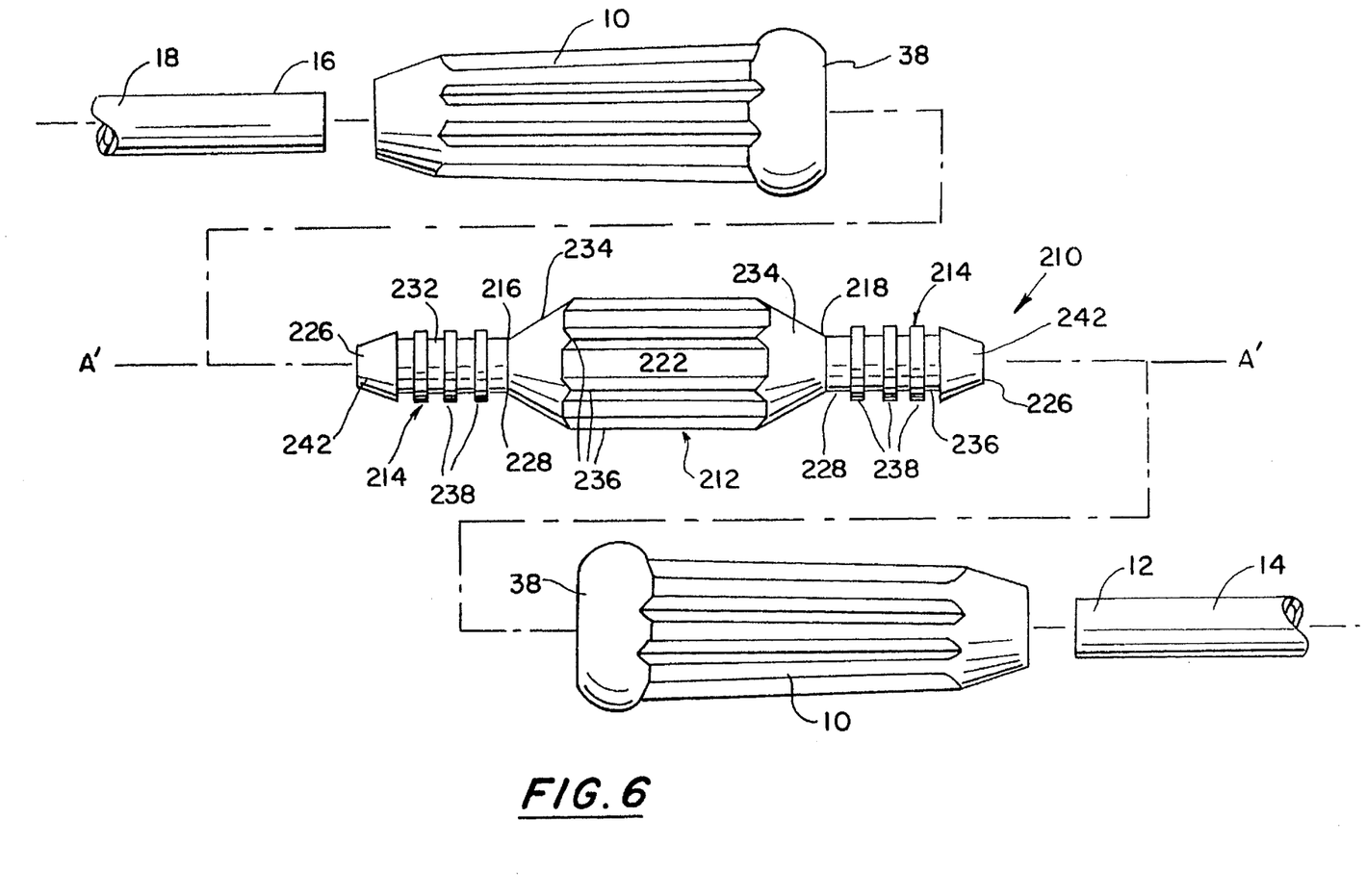
FIG. 6 is a side view in elevation of the first exemplary embodiment of the connector of the present invention shown in FIG. 5 with a pair of tubing end-pieces and a pair of free ends of tubing with each being disconnected from one another.
Figures 7, 9, 11:
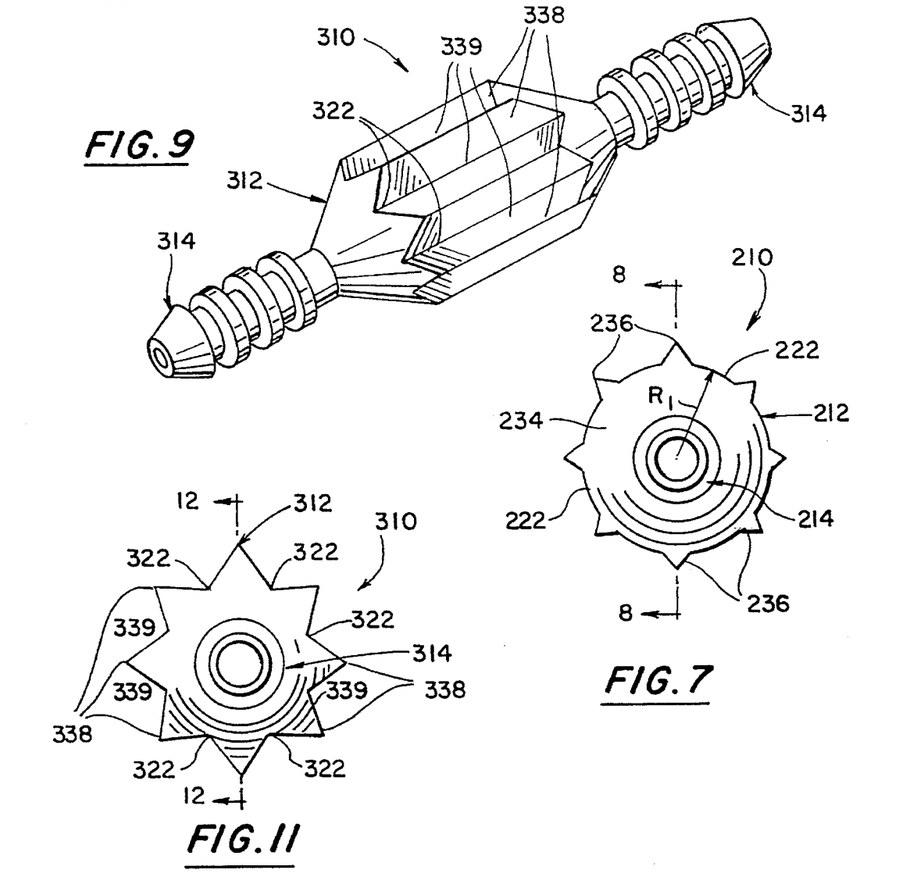
FIG. 7 is a front view and a rear view in elevation of the first exemplary embodiment of the connector of the present invention shown in FIG. 5.
FIG. 9 is a perspective view of a second exemplary embodiment of the connector of the present invention.
FIG. 11 is a front view and a rear view in elevation of the second exemplary embodiment of the connector of the present invention shown in FIG. 9.
Figure 8:
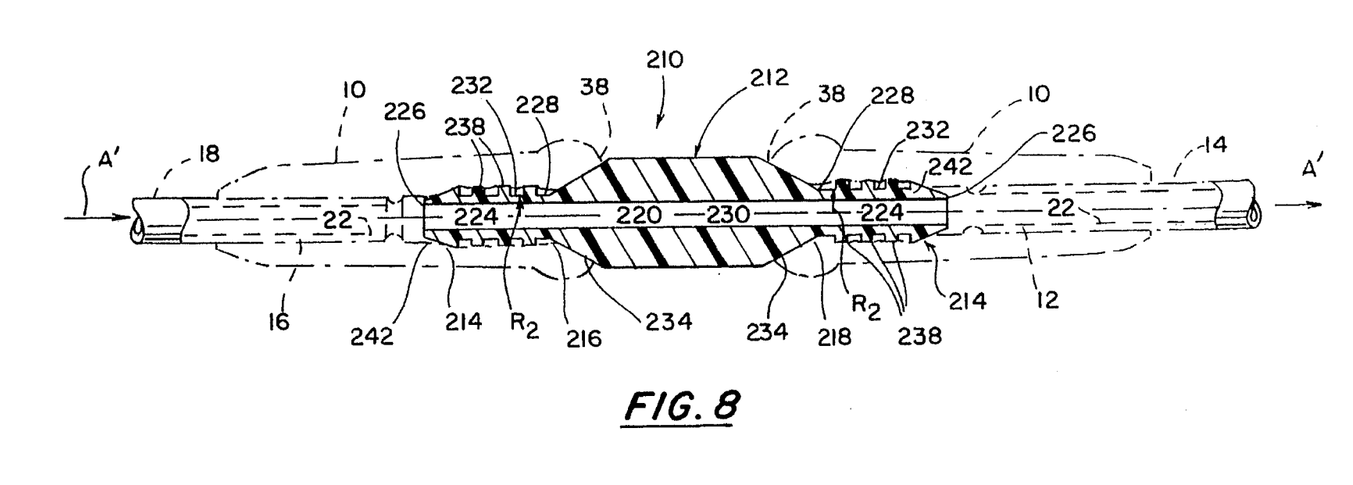
FIG. 8 is a side view in cross section of the first exemplary embodiment of the connector of the present invention taken along line 8—8 in FIG. 7 and illustrated interconnecting the pair of tubing end-pieces, drawn in phantom, connected to respective ones of the free ends of the tubing, also drawn in phantom, of FIG. 6.

Body structure 212 extends along a longitudinal axis "A'" from a first end 216 to a second end 218. As best shown in FIG. 8, body structure 211 has a hole 220 extending longitudinally therethrough and between first end 216 and second end 218. Hole 220 is oriented centrally about longitudinal axis "A'". As best shown in FIGS. 5–7, body structure 212 has an outer body surface 222 which extends longitudinally along and disposed radially from longitudinal axis "A'" at a first radial distance $R_1$.

As best shown in FIG. 8, each of tube structures 214 defines a conduit 224 which extends therethrough and each of tube structures 214 has a distal end 226 and a proximal end 228. Each of tube structures 214 is connected to a respective one of first and second ends 216 and 218 of body structure 212 at proximal end 228. When connected, each conduit 224 is oriented centrally about longitudinal axis "A'" so that conduits 224 and hole 220 form a continuous passageway 230 between distal ends 226 of the pair of tube structures 214 and through the pair of tube structures 214 and body structure 212. Each of tube structures 214 has an outer tube surface 232 which extends longitudinally along and radially from longitudinal axis "A'" at a second radial distance "$R_2$" as best shown in FIG. 8. To facilitate the ease of connecting or disconnecting connector 210 to the pair of tubing end-pieces 10, first radial distance "$R_1$" is greater than second radial distance "$R_2$" at least by a factor of 1.5, i.e. 1.5 times "$R_2$".

Body structure 212 is generally cylindrically shaped. Both body structure 212 and the pair of tube structures 214 are preferably fabricated of unitary construction. Also, body structure 212 and the pair of tube structures 214 are preferably fabricated from a stiff material such as plastic, fiberglass, wood or metal. Body structure 212 includes a pair of conical end portions 234. Each of conical end portions 234 tapers from outer body surface 222 towards a respective one of first and second ends 216 and 218. Body structure 212 includes a plurality of ridges 236 extending longitudinally along and projecting radially outwardly from outer body surface 222 relative to longitudinal axis "A'". Each of ridges 236 is configured in cross-section in a shape of an inverted "V" as best shown in FIG. 7.

Each of tube structures 214 includes a plurality of collars 238 which are connected to and extend circumferentially about and radially outwardly from outer tube surface 232. The plurality of collars 238 are spaced apart from one another to define an annularly-shaped channel 240, as best shown in FIG. 5, which is disposed between consecutive ones of collars 238. Each of said tube structures 214 also includes a frustoconically-shaped head member 242 which is disposed on and extends circumferentially about outer tube surface 232. Head member 242 commences at distal end 226 and diverges outwardly toward body structure 212. It is to be appreciated that each of the pair of tube structures 214 is operative to be removably inserted through first opening 38 and into bore 22 of a respective one of tubing end-pieces 10 so that connector 210 engages both of the tubing connectors 10 in a closely fitting relationship (as shown in FIG. 8) thereby enabling the fluid to flow between and through the respective pieces of tubing 14 and 18, as well as presenting a smooth nearly continuous exterior surface which resists snagging in use.

Figure 10:
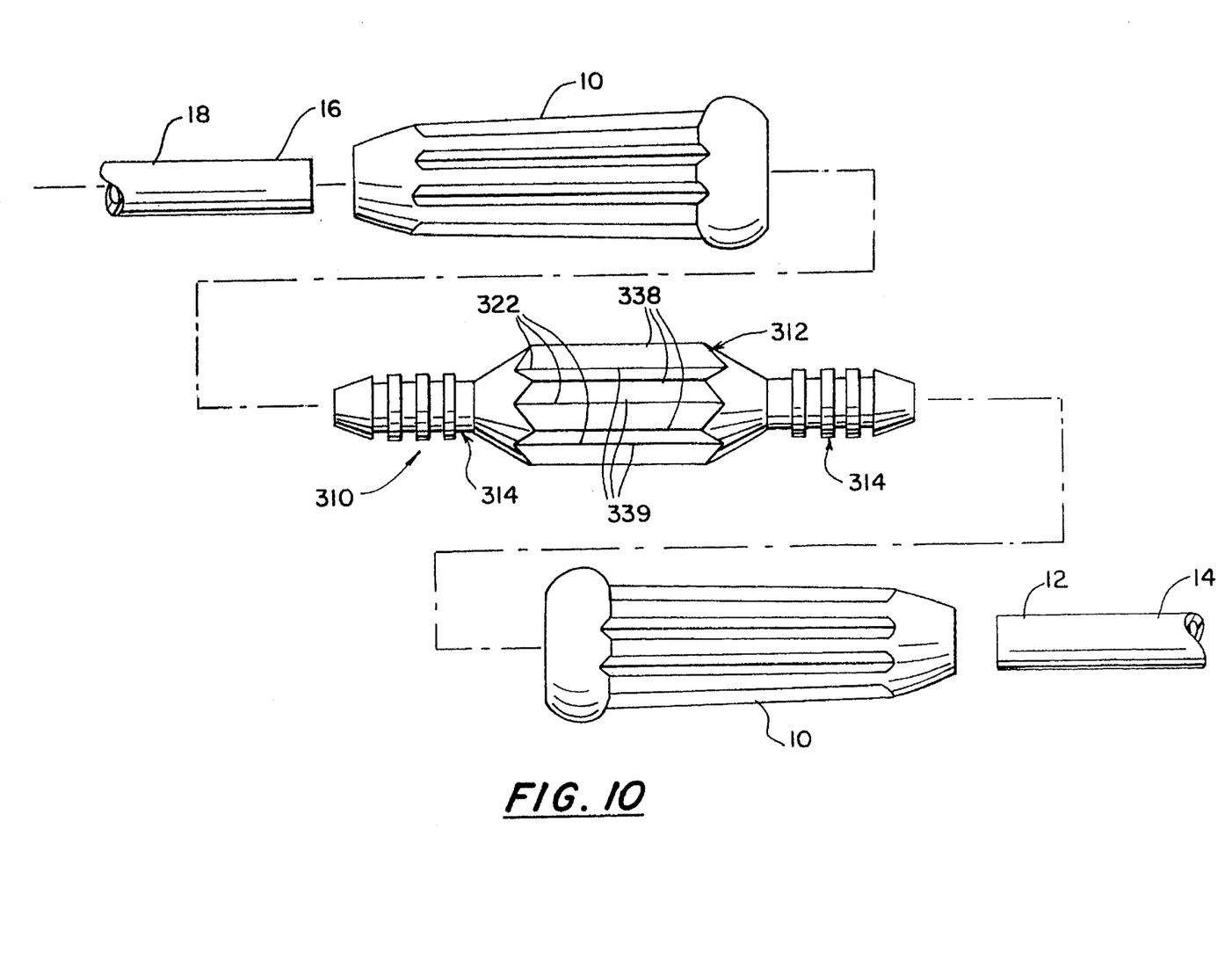
FIG. 10 is a side view in elevation of the second exemplary embodiment of the connector of the present invention shown in FIG. 9 with a pair of tubing end-pieces and a pair of free ends of tubing with each being disconnected from one another.
Figure 12:
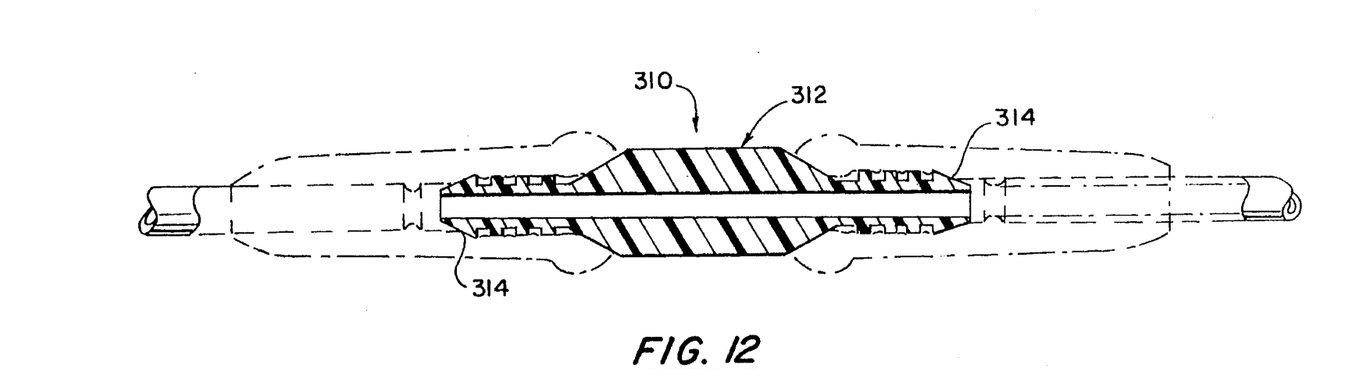
FIG. 12 is a side view in cross section of the second exemplary embodiment of the connector of the present invention taken along line 12—12 in FIG. 11 and illustrated interconnecting the pair of tubing end-pieces, drawn in phantom, connected to respective ones of the free ends of the tubing, also drawn in phantom, of FIG. 10.

A second exemplary embodiment of a connector 310 of the present invention is generally introduced in FIGS. 9–12. Features and benefits of this second exemplary embodiment of the connector 310 are substantially similar to those of the first exemplary embodiment. The only difference resides in a configuration of a plurality of ridges 338. Connector 310 includes a body structure 312 and a pair of tube structures 314. Outer body surface 322 is represented by a plurality of lines as shown in FIGS. 9–11. Each of ridges 338 is configured in cross-section in a shape of an inverted "V" as best shown in FIG. 11, and consecutive ones of the plurality of inverted V-shaped ridges 338 are spaced apart from one another by a V-shaped channel 339 which extends longitudinally along body structure 312.

Figure 13:
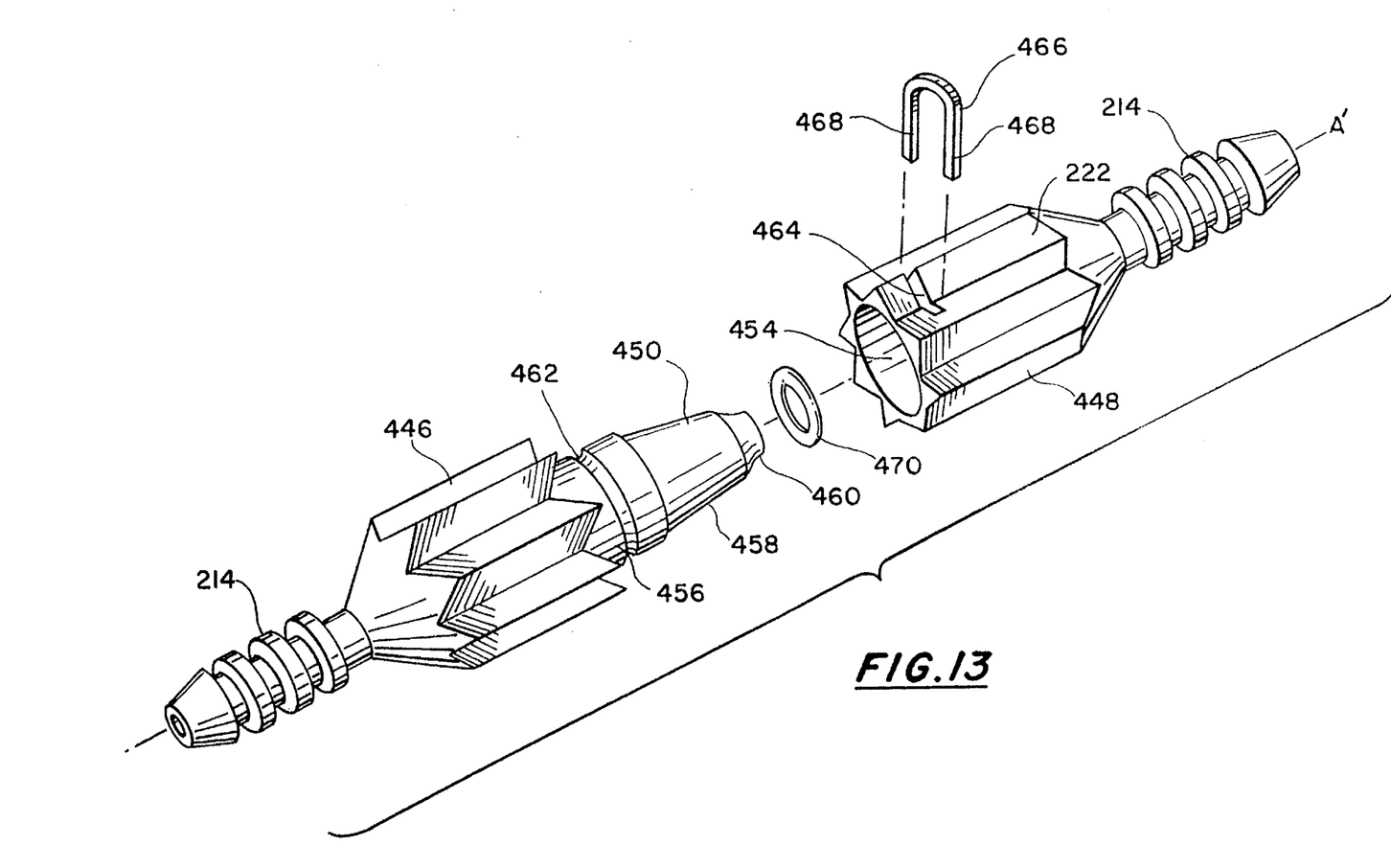
FIG. 13 is an exploded perspective view of a third exemplary embodiment of the connector of the present invention showing a first body member piece and a second body member piece which are releasably and rotatably connected to one another.

A third exemplary embodiment of a connector 410 is introduced in FIGS. 13–16. Connector 410 is similar to the connectors hereinabove described except that the body structure includes a first body member piece 446 and a second body member piece 448. First body member piece 446 and second body member piece 448 are releasably interconnected with one another and are operative to rotate about longitudinal axis "A'" relative to each other. One of first and second body member pieces 446 and 448 includes a tube stem 450 extending longitudinally and projecting outwardly therefrom in a direction opposite of a respective one of tube structures 214, as best shown in FIG. 13. Tube stem 450 has a tube stem conduit 452 extending therethrough and is disposed centrally about longitudinal axis "A'". A remaining one of first and second body member pieces 446 and 448 includes a tube stem bore 454 which is formed longitudinally thereinto along longitudinal axis "A'" and is sized and adapted to slidably and rotatably receive tube stem 450. Tube stem bore 454 extends partially through the remaining one of first and second body members 446 and 448 and disposed centrally about longitudinal axis "A'". By way of example only for the third embodiment of connector 410, first body member piece 446 has been selected to include tube stem 450 and second body member piece 448 has been selected to include tube stem bore 454 although a skilled artisan would appreciate that second body member piece 448 could have been selected to include tube stem 450 while first body member piece 446 would then include tube stem bore 454.

Figure 14:
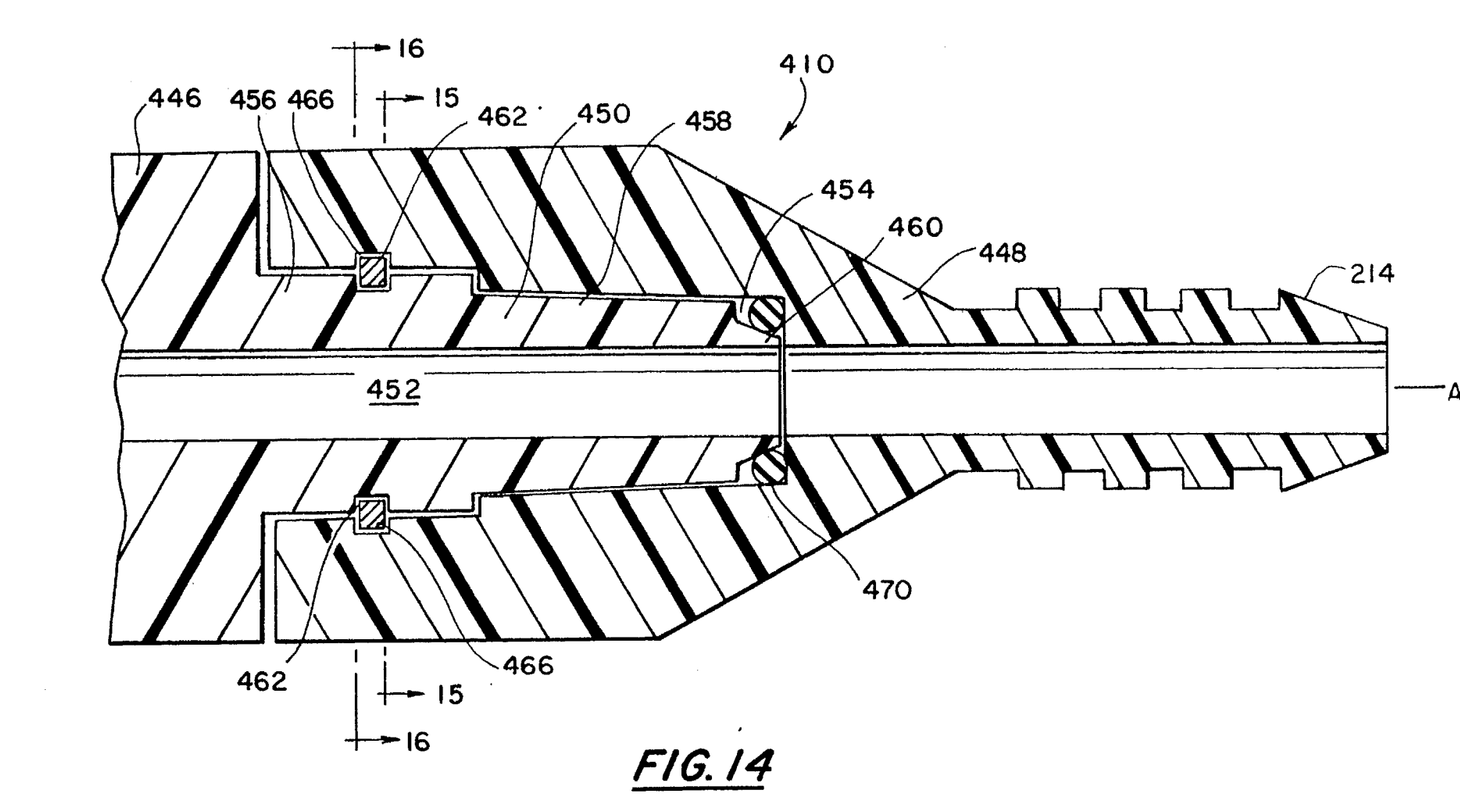
FIG. 14 is a side view in cross-section of the third exemplary embodiment of the connector of the present invention illustrating the interconnection between the first and second body member pieces with a seal element disposed therewith.
Figures 15, 16:
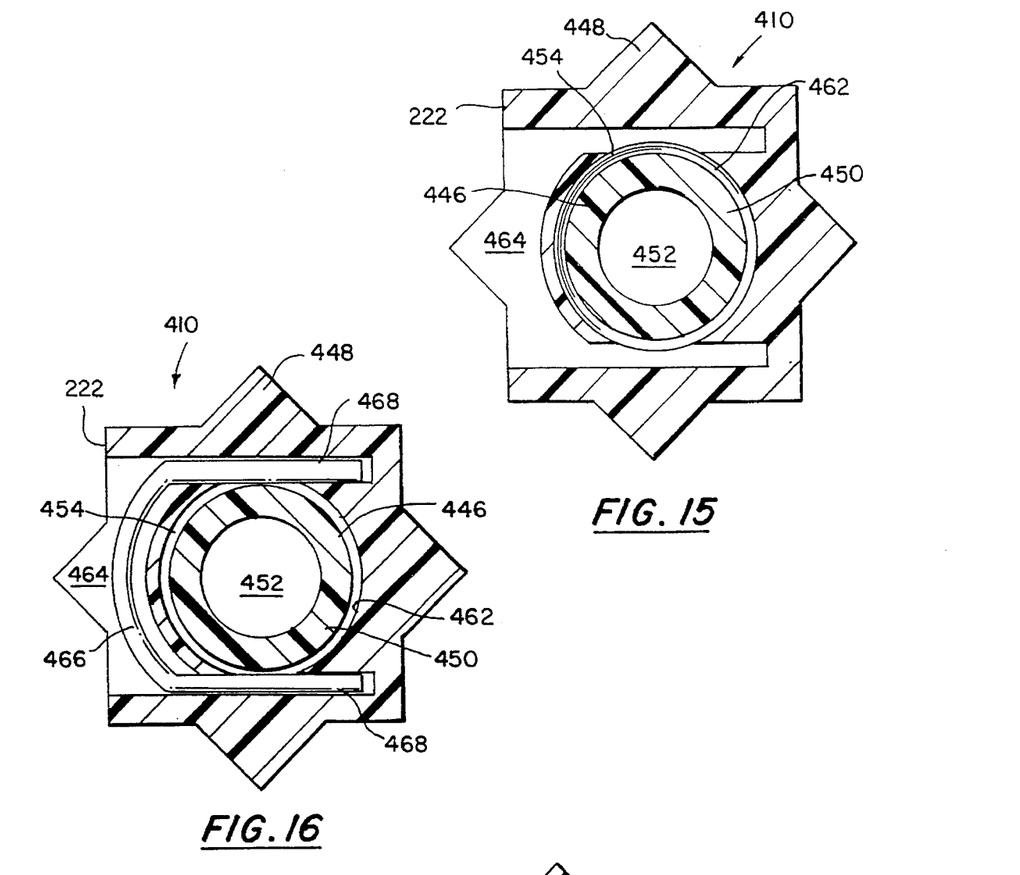
FIG. 15 is a side view in cross-section taken along line 15—15 in FIG. 14.
FIG. 16 is a side view in cross-section taken along line 16—16 of FIG. 14.

As best shown in FIGS. 13 and 14, tube stem 450 has a proximal cylindrical end portion 456, an intermediate conical portion 458 and a distal frustoconical nose portion 460. Tube stem bore 454 is a step-down bore which accommodates tube stem 450 for sliding and rotating therein in a close-fitting relationship. Tube stem includes a groove 462 which extends circumferentially around proximal cylinder end portion 456. As shown in FIGS. 13, 15 and 16, second body member piece 448, i.e. the remaining one of first and second body member pieces 446 and 448, includes a cavity 464 which extends transversely to longitudinal axis "A'" and from outer body surface 222 and in communication with tube stem bore 454.

Connector 410 of the third exemplary embodiment of the present invention includes a fastener 466 which is sized and adapted to be slidably received by cavity 464 in a close-fitting relationship as shown in FIG. 16. Fastener 466 is operative in conjunction with cavity 464 to engage a portion of groove 462 (FIGS. 14 and 16) so that first and second body members 446 and 448 are rotatably interconnected with one another. Fastener 466 has a pair of arms 468 which are disposed parallel with one another and are connected together in a manner to form a U-shaped clip element. Shown in FIGS. 14 and 16, each of arms 468 sized and adapted to engage a portion of groove 462 when fastener 466 is slidably received by cavity 464.

Figure 17:
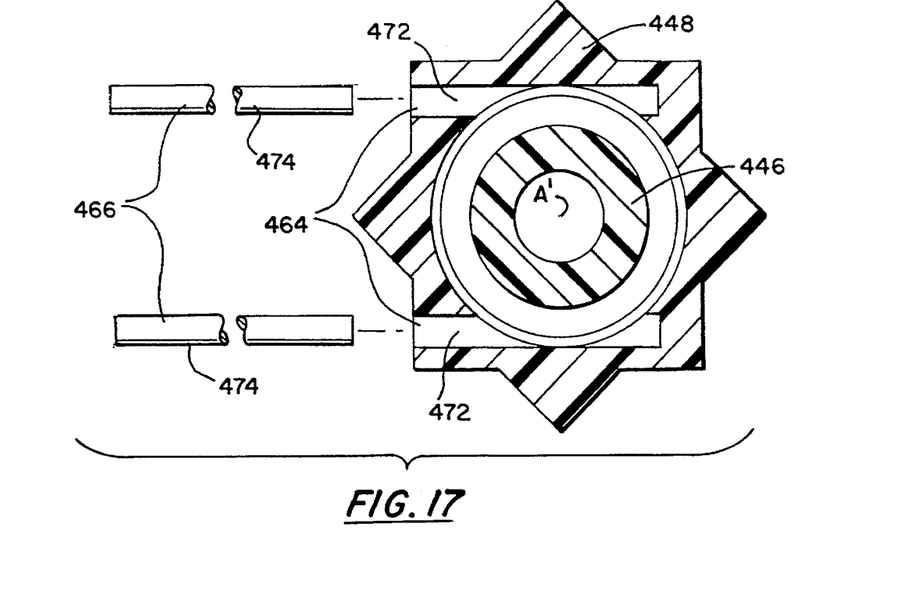
FIG. 17 is a side view in cross-section of the third exemplary embodiment of the connector showing an alternate means of releasably connecting the first and second body member pieces together.

As shown in FIG. 17, first body member piece 446 and second body member piece 448 are rotatably connected together in an alternative manner. Cavity 464 includes a pair of fastener holes 472 which are disposed parallel to one another and transverse to and on opposite sides of longitudinal axis "A'". Fastener 466 includes a pair of pins 474 which are sized and adapted to engage respective ones of fastener holes 272 in a mating relationship.

With reference to FIGS. 13 and 14, connector 410 of the third exemplary embodiment of the present invention also includes an annularly-shaped seal element 470. Seal element 470 is sized and adapted to be centrally positioned within tube stem bore 454 so that it surrounds longitudinal axis "A'" while being in contact with distal frustoconical nose portion 460 of tube stem 450 when tube stem 450 is rotatably received into tube stem bore 454. Seal element 456 is a common O-ring fabricated from a resilient material such as rubber or any other convention type of material commonly used for sealing purposes of this type.

Figure 18:
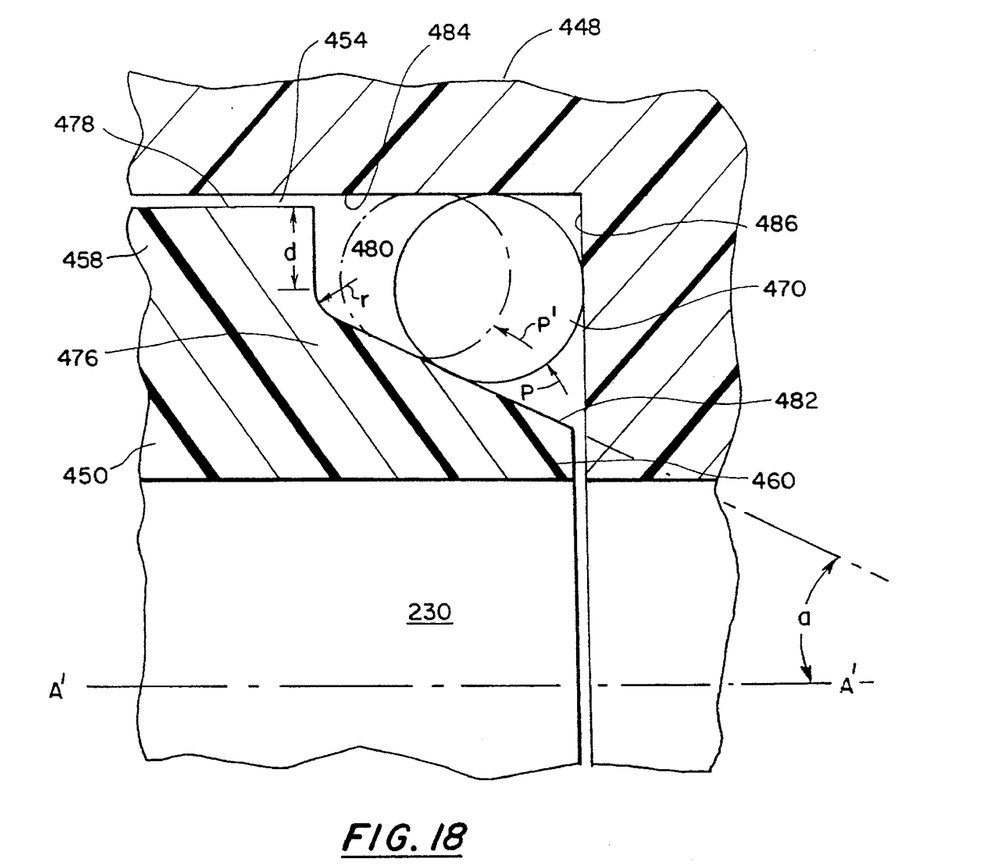
FIG. 18 is an enlarged partial side view in cross-section illustrating a seal element disposed between a tube stem of the first body member piece and a tube stem bore formed into the second body member piece.

In FIG. 18, intermediate conical portion of tube stem 450 and distal frustoconical nose portion 460 of tube stem 450 are joined together by a collar portion 476. In cross-section, collar portion 476 is formed with a radius "r" and is offset from an outer conical surface 478 a distance "d". Note that seal element 470 is nestled in an annular opening 480 and is in contact with an outer frustoconical surface 482 of distal frustoconical nose portion 460 and inner peripheral wall 484 and an inner radial wall 486 which, in part, defines tube stem bore 454. Outer frustoconical surface 482 tapers at an angle "a" relative to longitudinal axis "A'" which is preferably 20 degrees. As a result of nestling, seal element 470 provides adequate sealing of fluid flowing through continuous passageway 230 as long as the fluid flows under relatively low pressure indicated by pressure "P". Under higher pressure, indicated by "P'" seal element 470 tends to be displaced away from inner radial wall 486. However, simultaneously, seal element 470 becomes increasingly wedged between inner peripheral wall 484 and outer frustoconical surface 482 of distal frusto-conical nose portion 460 as illustrated in phantom. As a result of wedging, with increased fluid pressure, the sealing characteristics of seal element 470 also increases. A skilled artisan would appreciate that this feature can only operate within a reasonable zone of high pressures and that excessive pressures can possibly result in catastrophic failure of the connector of the present invention itself.

Figure 19:
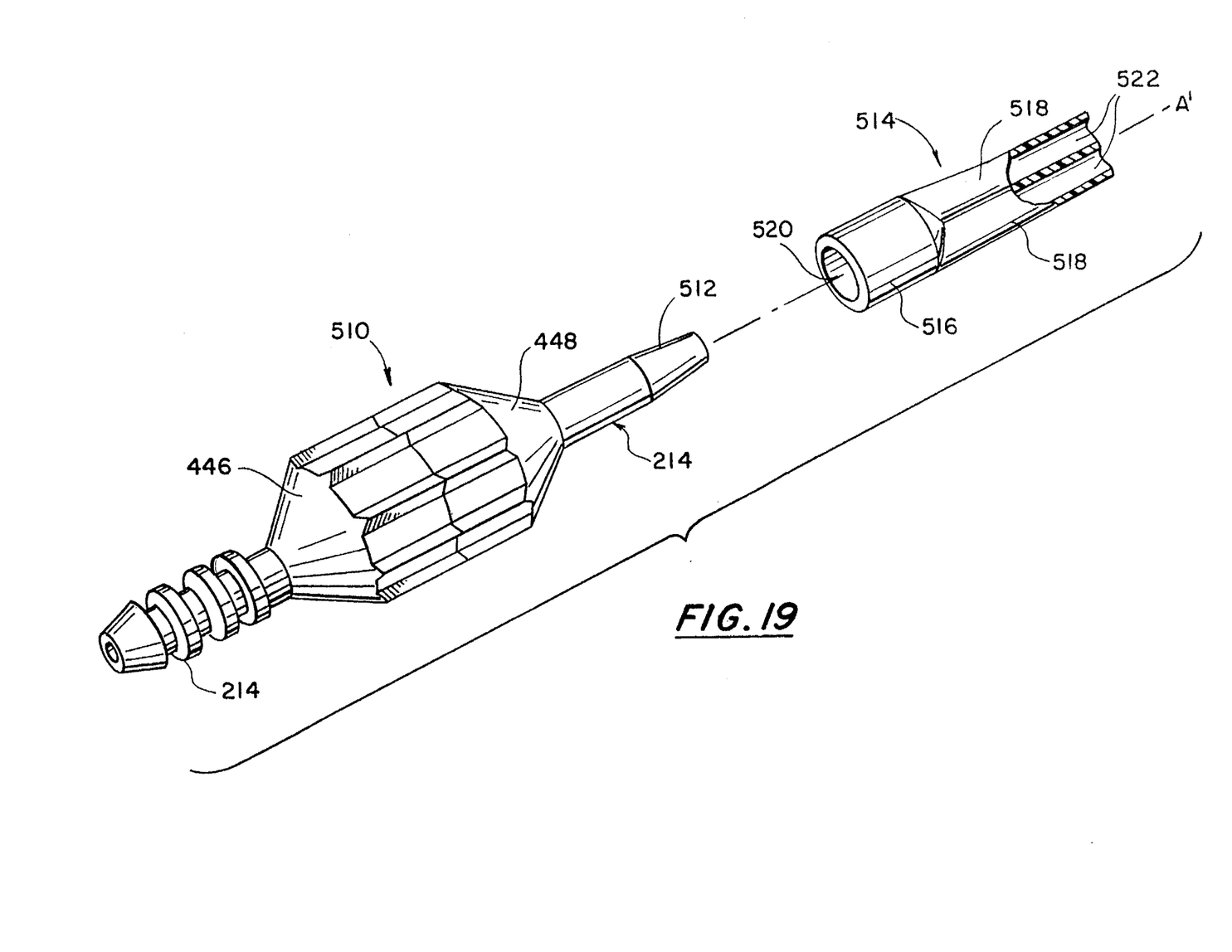
FIG. 19 is a perspective view of a fourth exemplary embodiment of the connector of the present invention and a splitter adapter for releasably connecting thereto.

FIG. 19 shows a fourth exemplary embodiment of a connector 510 of the present invention of a type whereby first body member piece 446 and second body member piece 448 can rotate relative to each other. One of tube structures 214 has a straight end 512 which is sized and adapted to receive a splitter adapter 514. Splitter adapter 514 includes a head member 516 and a pair of tube members 518. Head member 516 has a head conduit 520 formed therein that extends longitudinally and centrally about longitudinal axis "A'" and is sized and adapted to slidably receive straight end portion 512 in a matable relationship. Each of the pair of tube members 518 has a tubing conduit 522 that merges into head conduit 520 so that fluid flowing from connector 510 and into splitter adapter 514 can be divided into two separate flowing fluids. Conversely, two separate flowing fluids flowing from each tubing conduit 522 merge into one flowing fluid at head member 516.

The tubing end-piece and the combination of the tubing end-piece and connector provide numerous advantages and benefits. The tubing end-piece and combination of end-piece and connector are configured in, a manner to reduce the possibility of becoming caught with furniture, under doors or on other items. The tubing end-piece and end-piece connector have ends that are sufficiently rigid and configured in a manner so that, when urging the tubing end-piece onto a relatively rigid tubing connector or a fitting, the bore of the end-piece resists substantial deformation. The tubing end-piece as well as the connector have enhanced gripping characteristics so that each can be easily gripped when twisting onto or off of a each other or some other fitting. Both the tubing end-piece and the connector are effective in use and simple and inexpensive to manufacture.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A connector, comprising:
    (a) a generally cylindrically shaped body structure extending along a longitudinal axis from a first end to a second end and having a hole extending longitudinally through said body structure and between said first and second ends and being oriented centrally about said longitudinal axis, said body structure having an outer body surface extending longitudinally along and disposed radially from said longitudinal axis at a first radial distance and wherein said body structure includes a pair of conical end portions, each of said conical end portions tapering from said outer body surface towards a respective one of said first and second ends and wherein said body structure includes a plurality of ridges extending longitudinally along and projecting radially outwardly from said outer body surface relative to said longitudinal axis and each of said ridges is configured in cross-section in a shape of an inverted "V" and consecutive ones of said plurality of inverted V-shaped ridges are spaced apart from one another by a V-shaped channel extending longitudinally along said body structure; and
    (b) a pair of tube structures, each of said tube structures defining a conduit extending therethrough and having a distal end and a proximal end, each of said tube structures connected to a respective one of said first and second ends of said body structure at said proximal end whereby said conduit is oriented centrally about said longitudinal axis so that said conduits and said hole form a continuous passageway between said distal ends of said pair of tube structures and through said pair of tube structures and said body structure, each of said tube structures having an outer tube surface extending longitudinally along and radially from said longitudinal axis a second radial distance, said first radial distance being greater than said second radial distance.

2. In combination with a pair of tubing end-pieces, each of the tubing end-pieces connected to a respective free end of a piece of tubing and having an opening into a bore wherein a fluid can flow through the tubing end-piece and the piece of tubing, a connector adapted to interconnect the pair of tubing end-pieces so that the fluid can flow between and through the respective pieces of tubing, comprising:
    (a) a generally cylindrically-shaped body structure extending along a longitudinal axis from a first end to a second end and having a hole extending longitudinally through said body structure and between said first and second ends and being oriented centrally about said longitudinal axis, said body structure having an outer body surface extending longitudinally along and disposed radially from said longitudinal axis at a first radial distance and wherein said body structure includes a pair of conical end portions, each of said conical end portions tapering from said outer body surface towards a respective one of said first and second ends and wherein said body structure includes a plurality of ridges extending longitudinally along and projecting radially outwardly from said outer body surface relative to said longitudinal axis and each of said ridges is configured in cross-section in a shape of an inverted "V" and wherein consecutive ones of said plurality of inverted V-shaped ridges are spaced apart from one another by a V-shaped channel extending longitudinally along said body structure; and (b) a pair of tube structures, each of said tube structures defining a conduit extending therethrough and having a distal end and a proximal end, each of said tube structures connected to a respective one of said first and second ends of said body structure at said proximal end whereby said conduit is oriented centrally about said longitudinal axis so that said conduits and said hole form a continuous passageway between said distal ends of said pair of tube structures and through said pair of tube structures and said body structure, each of said tube structures having an outer tube surface extending longitudinally along and radially from said longitudinal axis a second radial distance, said first radial distance being greater than said second radial distance, each of said pair of tube structures operative to be removably inserted through the opening and into the bore of a respective one of the tubing end pieces to engage the tubing end pieces in a closely fitting relationship thereby enabling the fluid to flow between and through the respective pieces of tubing.

\* \* \* \* \*